(12) United States Patent
Withers et al.

(10) Patent No.: US 6,224,581 B1
(45) Date of Patent: May 1, 2001

(54) OSTOMY BAG CLEANING APPLIANCE HAVING A MOUNTING PLATE

(76) Inventors: Ginette Withers; Rod Withers, both of 622 Main Street, Lively, Ontario (CA), P3Y 1N1

( * ) Notice: Subject to any disclaimer, the term of this patent is extended or adjusted under 35 U.S.C. 154(b) by 0 days.

(21) Appl. No.: 09/448,601

(22) Filed: Nov. 24, 1999

(51) Int. Cl.⁷ .................................................. A61F 5/44
(52) U.S. Cl. ...................... 604/334; 604/332; 134/166 R
(58) Field of Search ................... 604/277, 317, 604/332, 334, 345; 134/166 C, 166 R, 169 AR (56) References Cited

U.S. PATENT DOCUMENTS

| | | | |
|---|---|---|---|
| 1,687,012 | * | 10/1928 | Forth . |
| 3,130,676 | * | 4/1964 | Beaulieu . |
| 3,990,909 | * | 11/1976 | Peckham ............................ 134/168 |
| 4,170,231 | | 10/1979 | Collins ................................ 128/283 |
| 4,194,506 | | 3/1980 | Voorhees ............................. 128/283 |
| 4,285,076 | * | 8/1981 | Dickstein .............................. 4/341 |
| 4,701,169 | | 10/1987 | Steer ................................... 604/344 |
| 4,766,622 | * | 8/1988 | Pacelli . |
| 5,037,408 | | 8/1991 | Henry ................................. 604/332 |
| 5,096,503 | * | 3/1992 | Wellman . |
| 5,333,630 | * | 8/1994 | Jepsen et al. . |
| 5,441,410 | * | 8/1995 | Segerdal . |
| 5,454,389 | * | 10/1995 | Hubbard et al. . |
| 5,503,633 | * | 4/1996 | Saunders et al. . |
| 5,573,187 | * | 11/1996 | Proctor . |
| 5,685,865 | * | 11/1997 | Cosgrove et al. . |
| 5,738,668 | | 4/1998 | Bugajski ............................. 604/332 |

FOREIGN PATENT DOCUMENTS

2258399 * 2/1993 (GB) .

* cited by examiner

*Primary Examiner*—Richard K. Seidel
*Assistant Examiner*—LoAn H. Thanh
(74) *Attorney, Agent, or Firm*—Bereskin & Parr (57) ABSTRACT

An ostomy bag cleaning appliance for cleaning an ostomy bag comprising a housing with a sealable top to prevent soiled water from splashing outside the cleaning appliance when in use, a mounting plate located within the housing for mounting a soiled ostomy bag, and a nozzle that projects through the mounting plate and into the mounted ostomy bag. A conventionally known attachment appliance which corresponds to the dimensions of the user's ostomy bag, can be affixed to the mounting plate so that an ostomy bag can be installed within the cleaning appliance. The head of the nozzle projects through an opening in the mounting plate and into the ostomy bag and provides a multi-directional stream of water into the ostomy bag. The nozzle provides a stronger flow of water downwards into the ostomy bag causing sufficient agitation to break up solid body waste within the ostomy bag. The outer diameter of the nozzle is smaller than the opening of the smallest ostomy bag, so that soiled water can flow back out of the ostomy bag and into the housing for a range of ostomy bag sizes. The appliance can also be used in association with an automatic controller for additional convenience, or in association with a portable water source for portable use.

15 Claims, 10 Drawing Sheets

OSTOMY BAG CLEANING APPLIANCE HAVING A MOUNTING PLATE

FIELD OF THE INVENTION

The present invention relates to the field of post-surgical apparatus, and more particulary to apparatus for the cleaning of ostomy bags.

BACKGROUND OF THE INVENTION

It is well known that many people are required to use body waste bags after undergoing colostomy, ileostomy, or other similar surgery on their intestinal or urinary tract. Subsequent to surgery, in which portions of the intestinal or urinary tract are removed, the waste products produced by the body are excreted at the residual opening, or stoma, formed in the abdominal wall. Excreta is typically collected by attaching an ostomy bag having a mating ring to an attachment appliance which is affixed to the outer side of the stoma. Such ostomy bags must be periodically evacuated and sanitized whenever the bag becomes partly filled with excrement, typically several times a day. While it is possible to simply remove and discard the ostomy bag each time the bag is soiled, it is not desirable for economical reasons. Further, it is not hygienically safe to dispose of a full ostomy bag into general waste facilities, and accordingly it is preferable to transfer the contents of an ostomy bag into a toilet facility.

Ostomy bag cleaning devices have been developed for the cleaning of ostomy bags, such as the device disclosed in U.S. Pat. No. 4,285,076 to Dickstein which provides a flexible tube mounted within a funnel-shaped pan which is used to provide flushing water into an ostomy bag for cleaning. However, this device can only practically be used to clean an ostomy bag that has a bottom opening and in use, will result in splashing of soiled water on the user. Further, this device does not provide the ability to clean an ostomy bag in a location other than home or hospital facility, in the case where an ostomy patient is otherwise healthy and able to travel.

Accordingly, there is a need for an ostomy bag cleaning appliance which provides hygienic and efficient cleaning of an ostomy bag, which is convenient and easy to operate, and which can be adapted for portable use.

BRIEF SUMMARY OF THE INVENTION

It is therefore an object of the present invention to provide an ostomy bag cleaning appliance for cleaning an ostomy bag having a stoma mating ring, said cleaning appliance comprising:

(a) a housing having an interior, the housing comprising an accessible upper portion having an inside surface and a lower portion configured to direct soiled water out of said housing;

(b) an engagement device coupled to said housing for engaging the stoma mating ring of the ostomy bag, the engagement device having an aperture in fluid communication with the interior of the housing; and (c) a cleaning nozzle mounted within said housing and extending through said aperture of said engagement device, such that when the stoma mating ring is engaged with said engagement device, said nozzle extends into the ostomy bag through said aperture.

Further objects and advantages of the invention will appear from the following description, taken together with the accompanying drawings.

DETAILED DESCRIPTION OF PREFERRED EMBODIMENTS

Figure 1A:
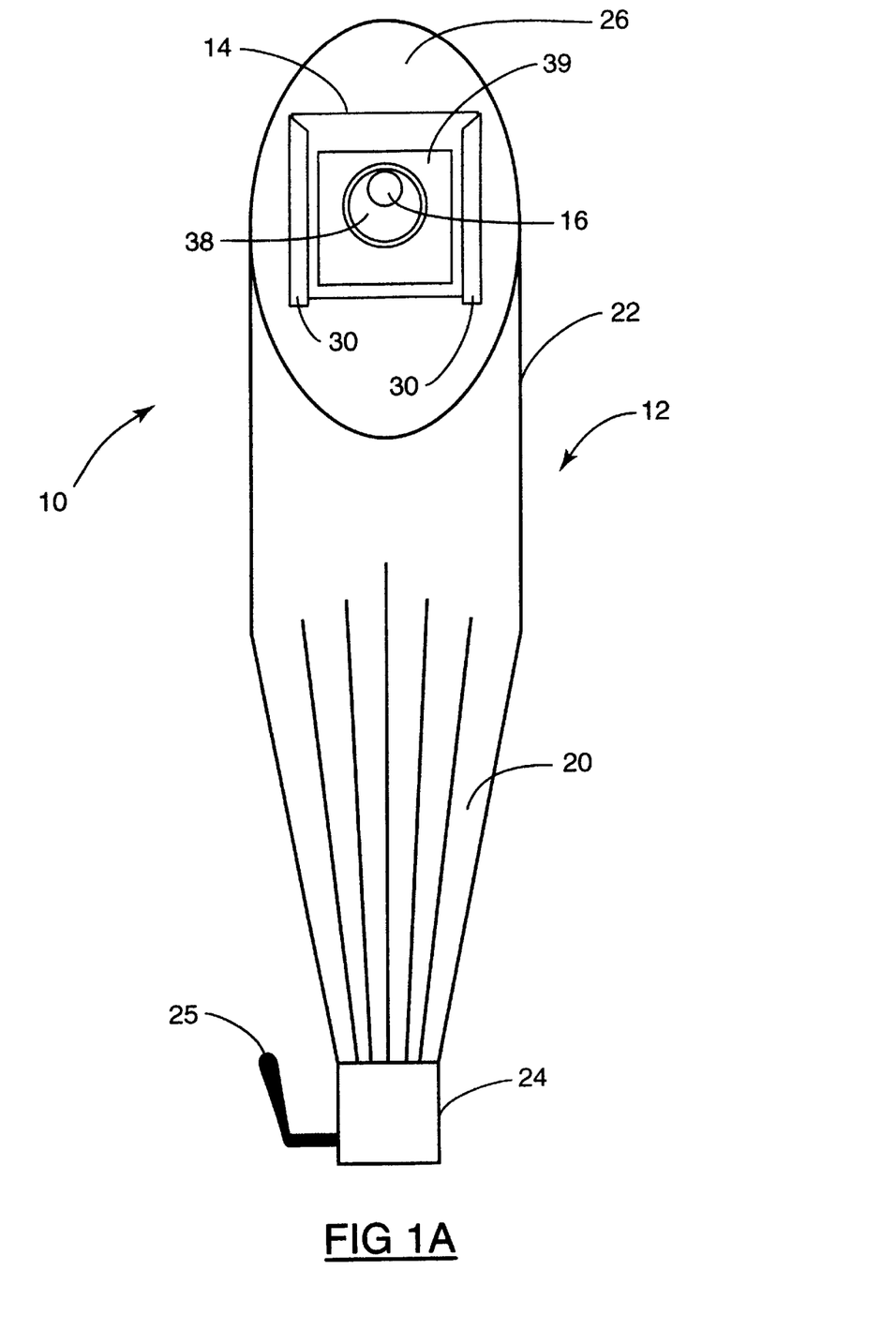
FIG. 1A is a front view of an ostomy bag cleaning appliance according to a preferred embodiment of the present invention.
Figure 1B:
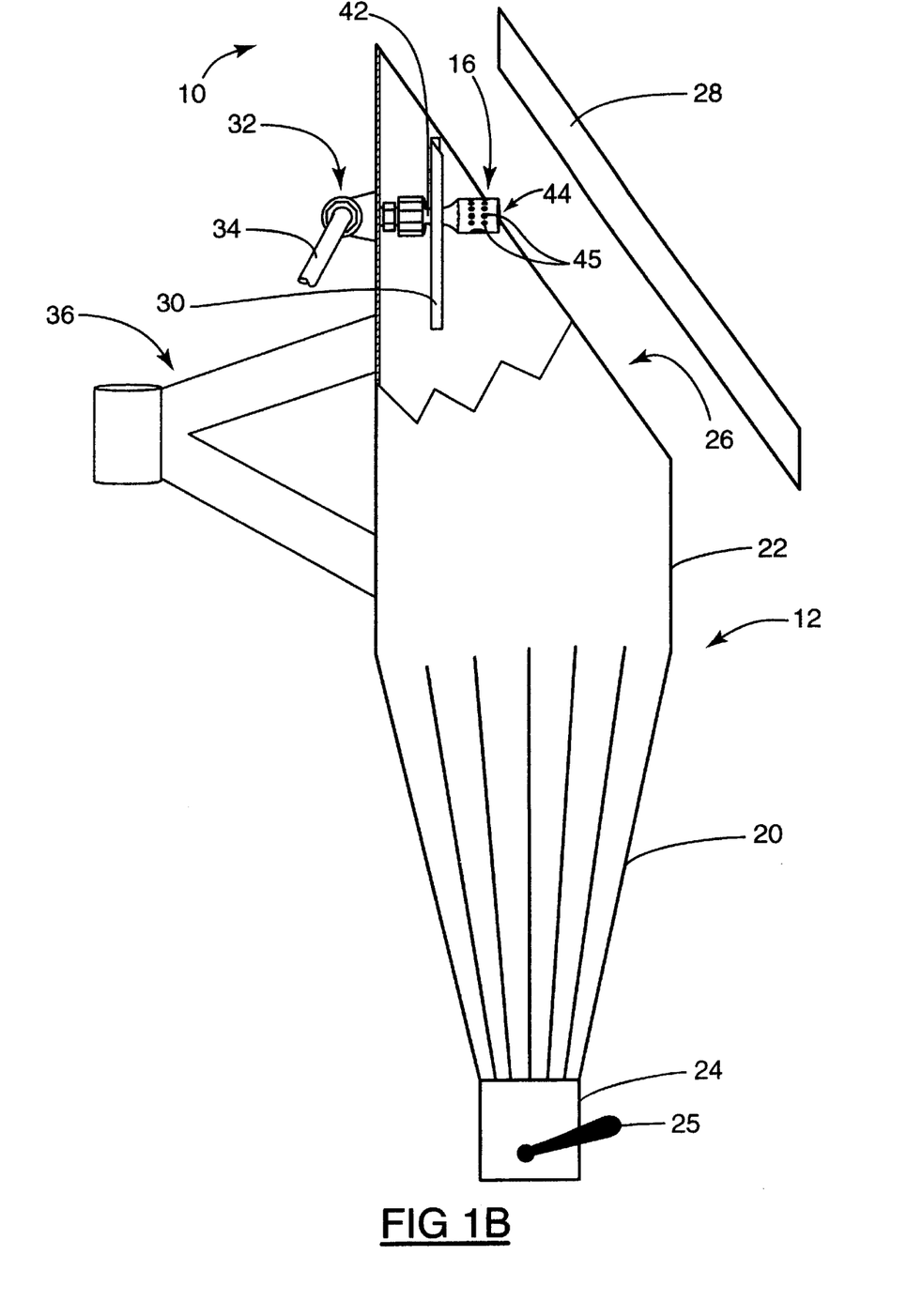
FIG. 1B is a partially cut-away side view of the cleaning appliance of FIG. 1A.
Figure 1C:
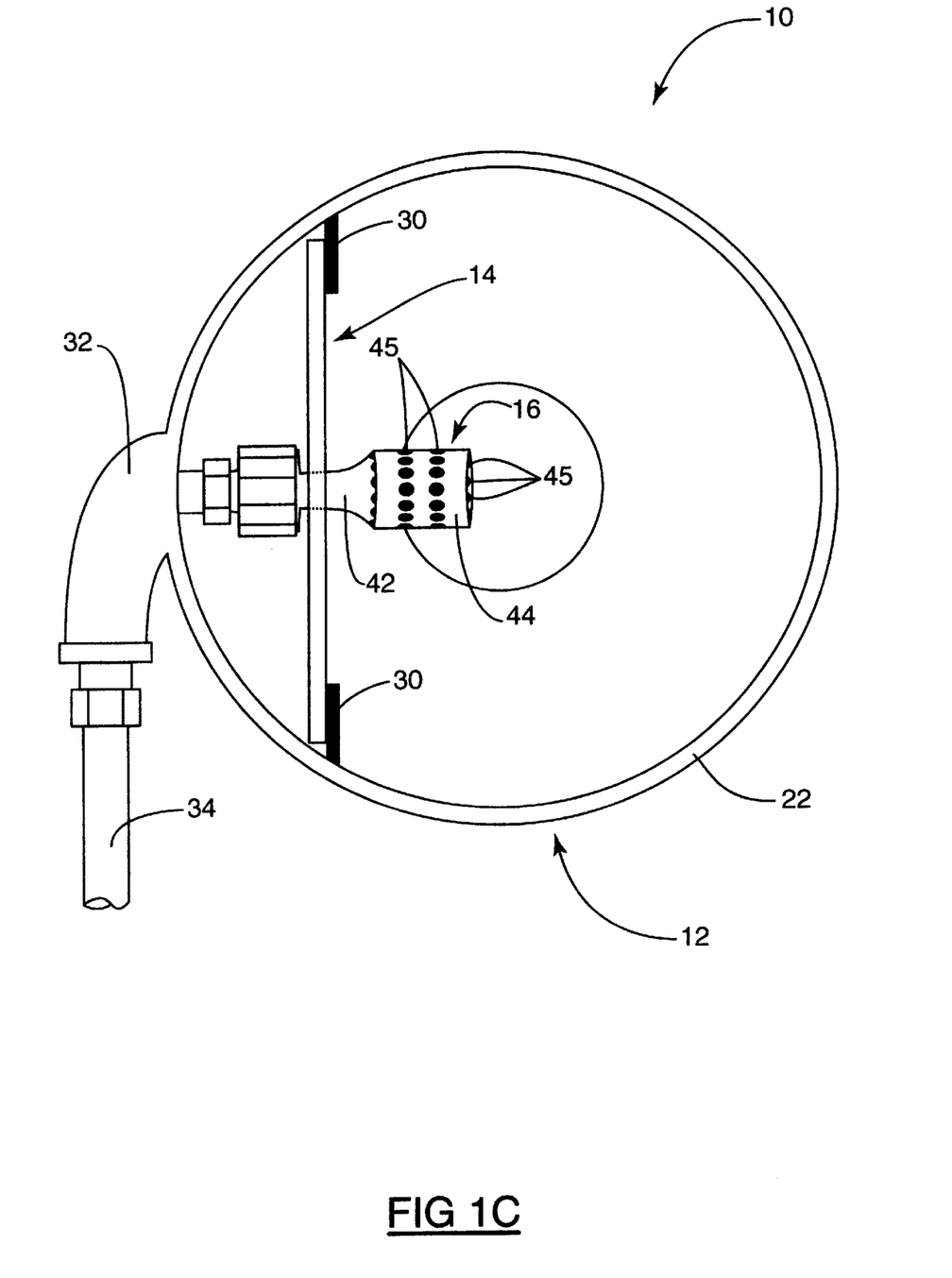
FIG. 1C is a top plan view of the cleaning appliance of FIG. 1A.

Reference is first made to FIGS. 1A, 1B, and 1C which show front, side and top views of the ostomy bag cleaning appliance 10, made in accordance with a preferred embodiment of the invention. Cleaning appliance 10 comprises a housing 12 for housing the ostomy bag, a mounting plate 14 for securing the ostomy bag within cleaning appliance 10, and a nozzle 16 for providing a multi-directional water flow to the inside of an ostomy bag in order to loosen and flush out waste contained within the ostomy bag. For ease of understanding, the term "ostomy bag" is hereinafter used to indicate any type of ostomy bag, including but not limited to, colostomy bags, ileostomy bags and the like.

Housing 12 has a funnel-shaped lower portion 20 and a substantially cylindrical upper portion 22. Lower portion 20 terminates in an outlet valve 24 having a handle 25 to allow the user to control the delivery of soiled water flow into a toilet below (not shown). The upper portion 22 of housing 12 has an open top 26 through which the user can reach to install an ostomy bag within the cleaning appliance. A lid 28 (FIG. 1B) which is adapted to fit snugly on top of open top 26, is used to create a spill-proof seal to prevent spillage when an ostomy bag is being washed within cleaning appliance 10. Lid 28 (FIG. 1B) and housing 12 are made of a suitable corrosion resistant metal (e.g. stainless steel).

A pair of mounting brackets 30 (FIG. 1A) are welded to the inside back wall of housing 12, near the top of housing 12 and are adapted to receive mounting plate 14. Plumbing fixture 32 (FIGS. 1B and 1C) is extends through the back wall of housing 12. A conventional water pipe 34 may be coupled to the plumbing fixture 32 to provide a water flow into cleaning appliance 10 from a conventional bathroom water supply. A support member 36 (FIG. 1B) is provided on the outer back surface of upper portion 22 which allows for the attachment of cleaning appliance 10 onto a support pole (not shown) so that cleaning appliance 10 can be moved from a storage position away from the toilet to an operational portion over a toilet.

Mounting plate 14 is generally flat and adapted to be slideably received within mounting brackets 30. Mounting plate 14 has an opening 38 which is sized so that a variety of different sized attachment appliances 39 can be attached to mounting,plate 14 over opening 38 and be supported by the edges of mounting plate 14 surrounding opening.38. Once a user attaches one of his/her own attachment appliances 39 onto mounting plate 14 and installs mounting plate 14 within cleaning appliance 10, the user's ostomy bag (not shown) can be easily installed onto, and removed from, mounting plate 14 inside cleaning appliance 10. Mounting plate 14 can be manufactured out of any rigid impervious material (e.g. rigid plastic or metal).

Nozzle 16 is coupled to plumbing fixture 32 and is used to direct a flow of water inside an ostomy bag. Nozzle 16 has a stem 42 and a head 44 and is positioned within opening 38 of mounting plate 14 such that head 44 of nozzle 16 projects past opening 38. Stem 42 includes an inside threaded surface (not shown) which is sized to engage a mating threaded outside surface (not shown) of plumbing fixture 32. Head 44 contains a number of apertures 45 on its various surfaces which provide a multi-directional flow of water into cleaning appliance 10. It should be understood that mounting plate 14 must be first inserted within mounting brackets 30 before nozzle 16 can be coupled to plumbing fixture 32. Nozzle can be manufactured out of any corrosive resistant metal (e.g. copper).

Figure 2A:
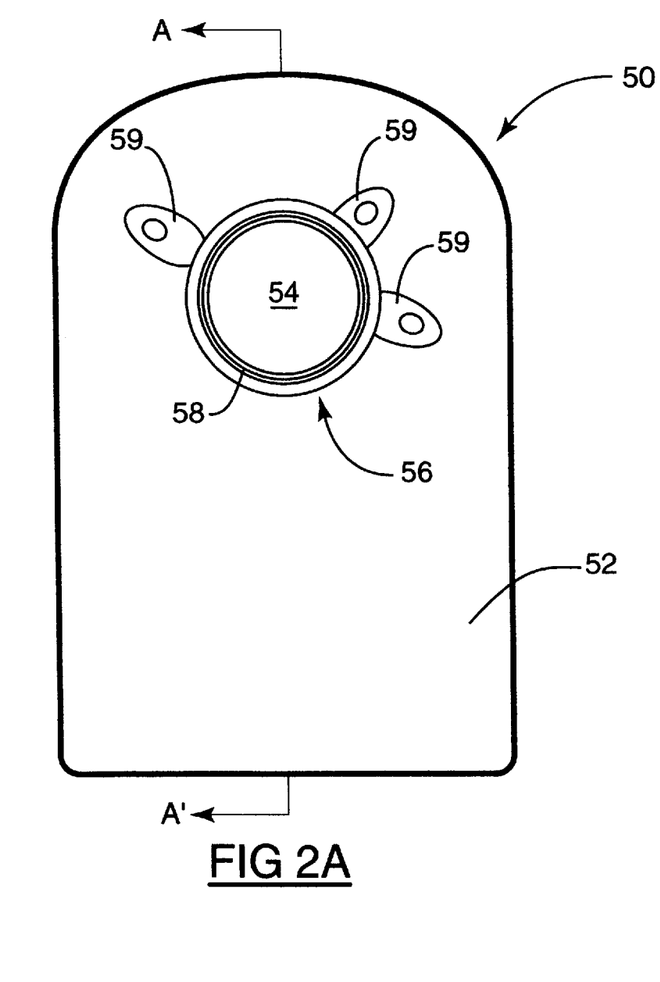
FIG. 2A is a front view of a typical ostomy bag which may be used in association with the cleaning appliance of the present invention.
Figure 2B:
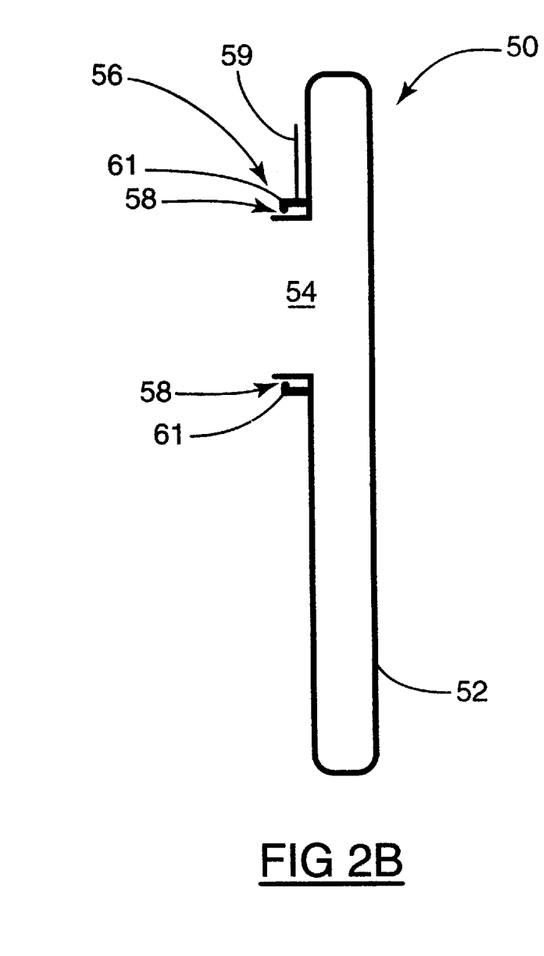
FIG. 2B is a sectional view taken along the line A–A' of FIG. 2A.

Referring now to FIGS. 2A and 2B, a typical ostomy bag 50 is shown comprising a flexible thin plastic pouch 52 made of an impermeable plastic material (e.g. polyvinylchloride) and which is formed to lie generally flat against the body. Ostomy bag 50 has a stomal orifice 54 which is surrounded by a stoma mating ring 56 of semi-rigid plastics material (e.g. polyethylene). Stoma mating ring 56 has a grooved interior 58 and a locking rib 61 on the inside surface of the outer wall of grooved interior 58, both of which run along the full extent of its periphery.

Stoma mating ring 56 typically includes several belt tabs 59 mounted along the sides of stoma mating ring 56 for use with an ostomy bag support belt (not shown), as is conventionally known. Tabs 59 can also be grasped by the user to assist in engaging it with, and disengaging it from, an attachment appliance (not shown), which is used to adhere ostomy bag 50 to the skin of a user, as is conventionally known.

Figures 3A, 3B:
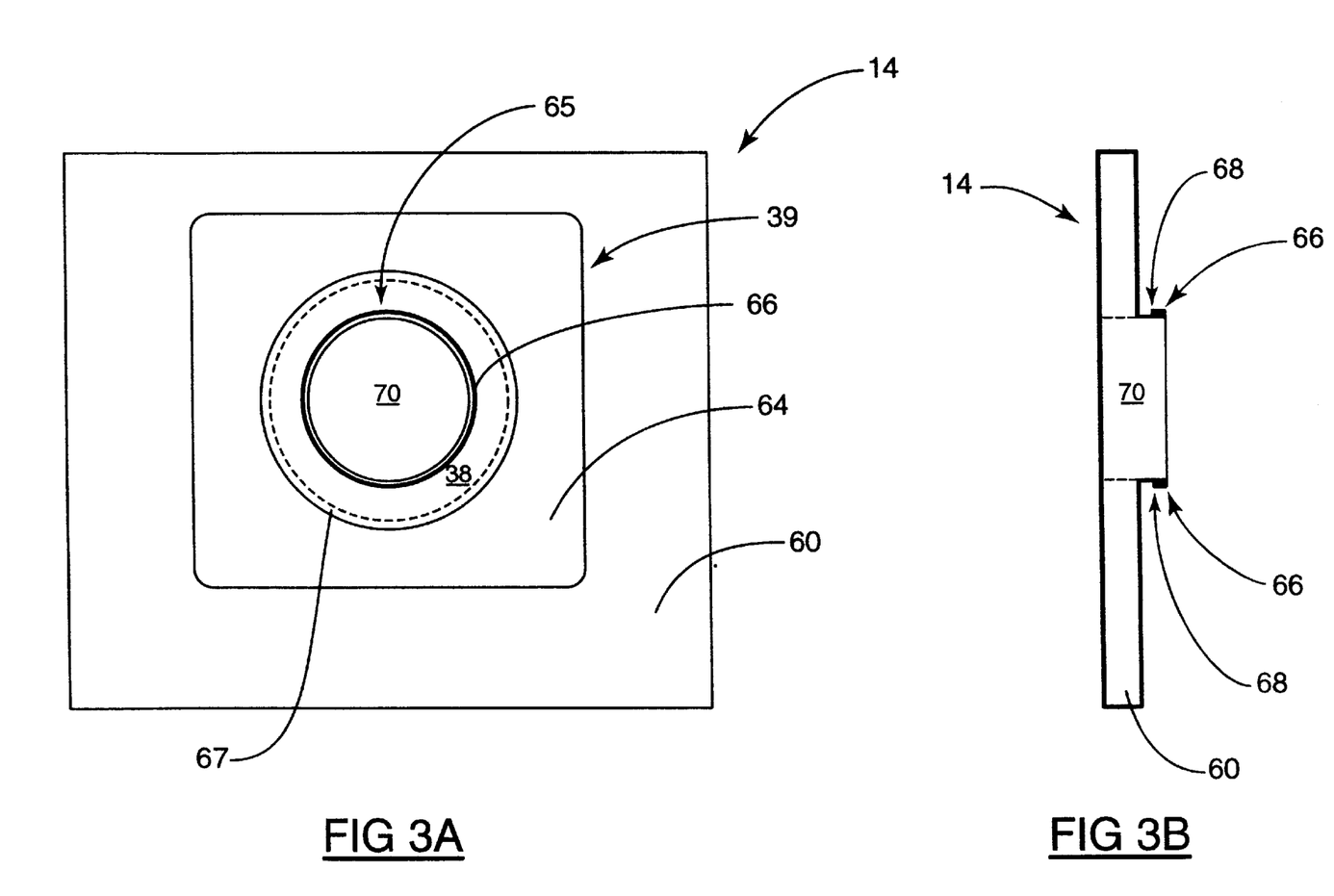
FIG. 3A is a front view of the mounting plate of the cleaning appliance of FIG. 1A.
FIG. 3B is a partial cross-sectional side view of the mounting plate of FIG. 3A.

FIGS. 3A and 3B show detailed views of mounting plate 14 which comprises a rigid plastic plate 60 having opening 38 (shown in dotted outline). Mounting plate 14 is shown having an attachment appliance 39 affixed to the front surface of plastic plate 60 over opening 38. Attachment appliance 39 is well known, and comprises a medical grade adhesive pad 64 (which is normally used to adhere attachment appliance 39, and thus ostomy bag 50 to a user's body), and an annular collar 65 of semi-rigid plastics material (e.g. polyethylene) which is permanently formed with adhesive pad 64.

Collar 65 includes a flange 66 that extends away from the front surface of collar 65 in a lateral direction and defines an aperture 70. Flange 66 forts an inner peripheral recess 68 that extends around the inside surface of flange 66 and which is of a size and shape that corresponds to the size and shape of the grooved interior 58 of stoma mating ring 56 of ostomy bag 50.

Accordingly, stoma mating ring 56 can be snap-fit within collar 65 of attachment appliance 39 which is attached to mounting plate 14. Specifically, rib 61 of stoma mating ring 56 can be releaseably engaged within peripheral recess 68 of attachment appliance 39 to provide a substantially leakproof seal therewith. Generally, the diameter of rib 61 of stoma mating ring 56 is designed to be from 2 to 10% smaller than the diameter of recess 68 of the corresponding attachment appliance 39 to provide a close fit therebetween and such that ostomy bag 50 can be securely coupled to mounting plate 14 in an air-tight manner, as is conventionally known.

It is preferred that collar 65 have an outer diameter which is slightly larger than opening 38 of plastic plate 60, so that collar 65 is supported by a support ledge 67 of plastic plate 60 which borders opening 38. This allows the user to attach an ostomy bag 50 to attachment appliance 39 with greater ease. Further, each individual user has a uniquely sized stoma opening which requires a uniquely sized stoma mating ring 56 and attachment appliance aperture 70. Accordingly, it is necessary to ensure that collar 65 has an outer diameter which is slightly larger than opening 38 of plastic plate 60 for a number of different attachment appliances 39.

By designing opening 38 to have a diameter which is slightly smaller than the outside diameter of collar 65 of the smallest conventional attachment appliance 39, a range of attachment appliances 39 can be accommodated by mounting plate 14 and the corresponding ostomy bags 50 can be cleansed within cleaning appliance 10. For example, for an attachment appliance 39 having a collar 65 with an outer diameter of approximately 6 centimeters and an aperture 70 of approximately 3.5 centimeters, a mounting plate 14 with an opening 38 of diameter of approximately 5.5 centimeters would provide a sufficiently deep wide support ledge 67 (e.g.0.5 centimeters) to support collar 65.

Figure 4:
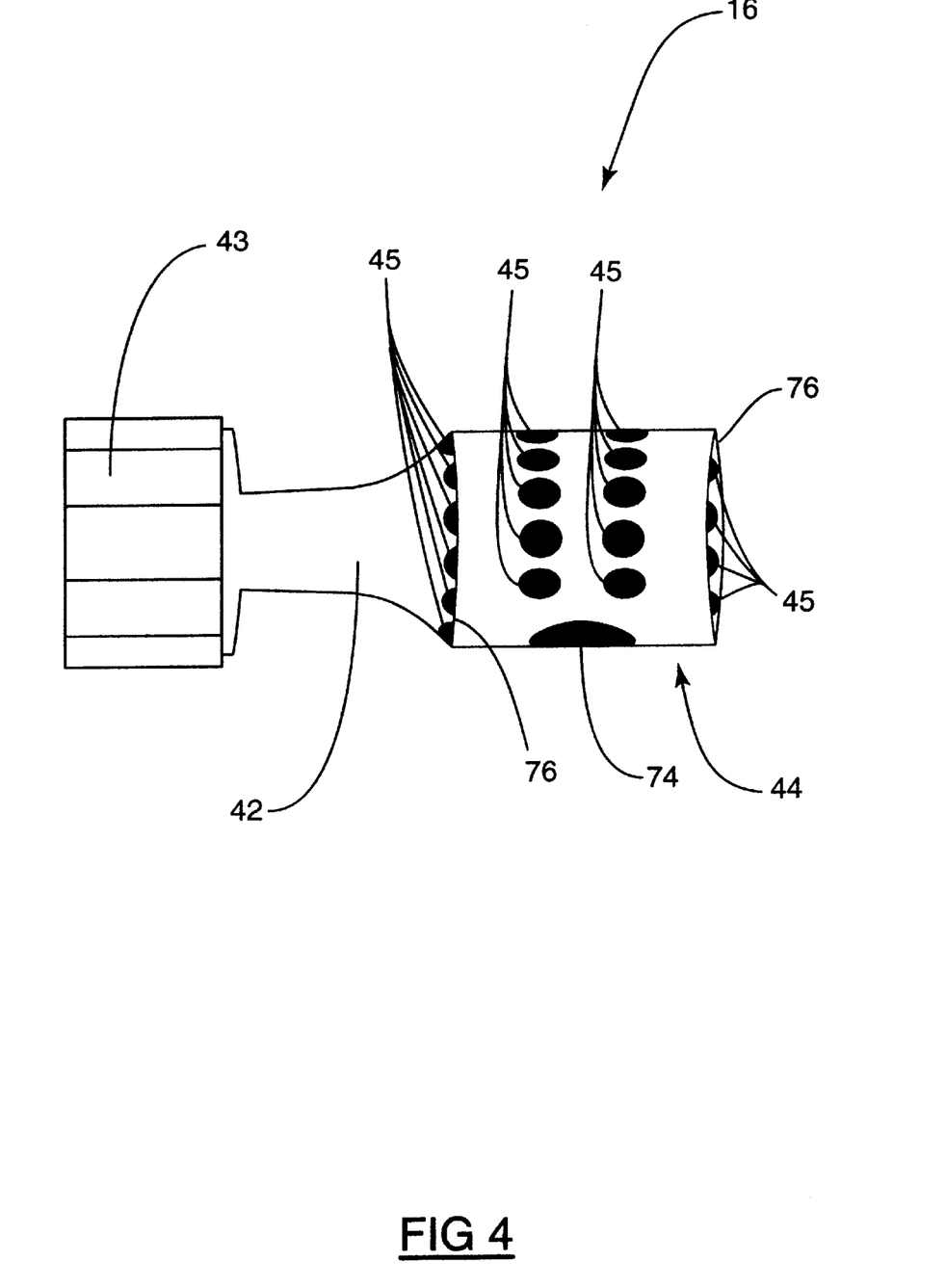
FIG. 4 is a side perspective view of the nozzle of the cleaning appliance of FIG. 1A.

FIG. 4 shows a detailed view of nozzle 16 which contains a plurality of apertures 45 located on a number of surfaces of its head 44. A relatively large aperture 74 is located on the underside of the head 44, to provide a strong flow of water downwards. Apertures 45 are provided all around the side surface as well as along the two rims 76 of head 44 to facilitate a multi-directional flow of water through nozzle 16. Stem 42 terminates at one end in a threaded connector 43 having an inner threaded surface (not shown) which is adapted to couple nozzle 16 to plumbing fixture 32 (FIG. 1B) of housing 12.

Stem 42, connector 43 and head 44 must have an outer diameter which is substantially smaller than the diameter of opening 38 of mounting plate 14. This is to ensure that head 44 of nozzle 16 can pass through opening 38 of mounting plate 14 and into ostomy bag 50 when installed within cleaning appliance 10. Further, stem 42 must have an outer diameter which is substantially smaller than the diameter of the aperture 70 of the smallest attachment appliance 39 being accommodated. This ensures that sufficient air space is provided between the outside surface of stem 42 and the inside surface of flange 66 of attachment appliance 39 to allow soiled water to be flushed back through stoma orifice 54 of ostomy bag 50, aperture 70 of attachment appliance 70 and into the interior of housing 12, when flushing water is provided through nozzle 16 into ostomy bag 50.

In the previously cited example where a typical collar 65 has an aperture 70 of diameter of 3.5 centimeters, a suitable nozzle would have a stem 42 with a diameter of approximately 1 centimetre, to provide sufficient clearance therebetween for drainage of soiled water back through stoma orifice 54 of ostomy bag 50.

Figure 5A:
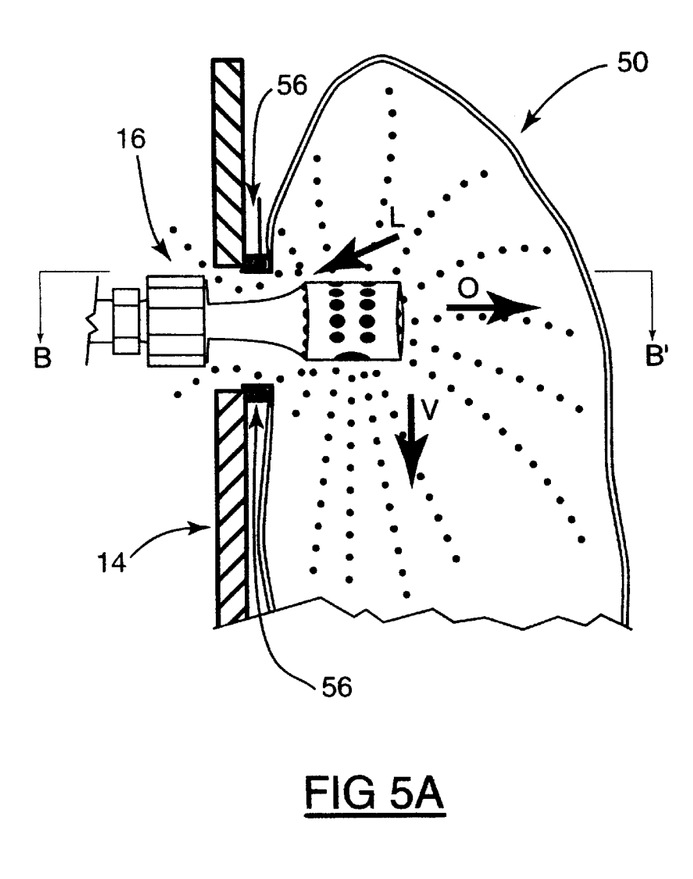
FIG. 5A is a partial cross-sectional view of the mounting plate and nozzle of FIG. 1A in association with the ostomy bag of FIG. 2A.
Figure 5B:
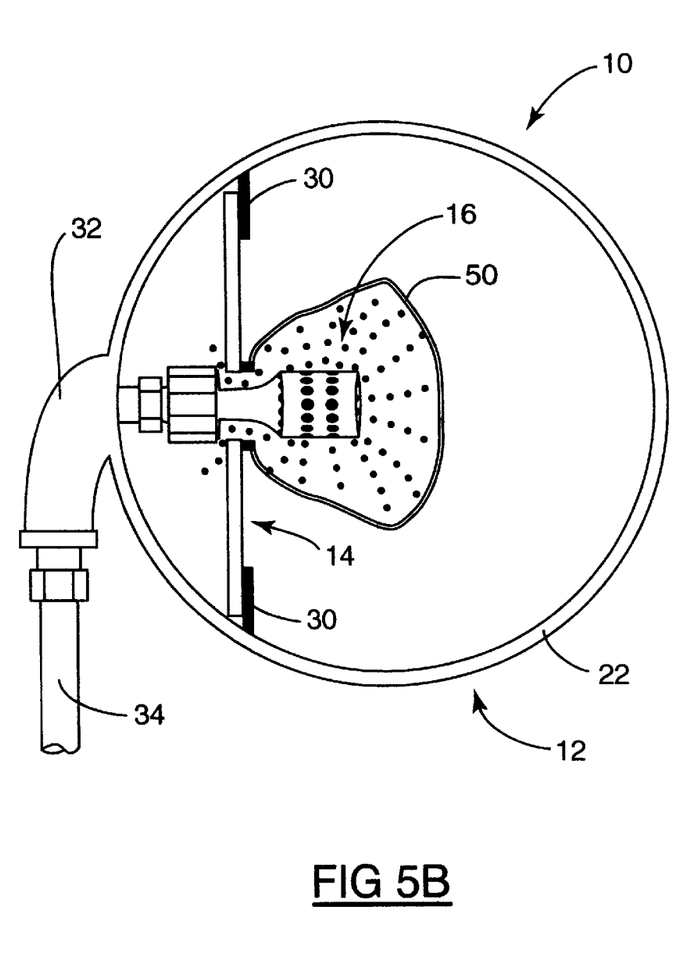
FIG. 5B is a sectional view taken along the line B–B' of FIG. 5A.

FIGS. 5A and 5B show side cross-sectional view and a top view of mounting plate 14 and nozzle 16 in association with ostomy bag 50. As discussed, when stoma mating ring 56 of ostomy bag 50 is installed onto attachment appliance 39 of mounting plate 14, nozzle 16 will extend into the body of ostomy bag 50. When flushing water is provided from water pipe 34 through nozzle 16 into ostomy bag 50, a multi-directional flow of water is provided in various directions which assists in cleansing all inner surfaces of ostomy bag 50. Specifically, water flow can extend vertically in the direction shown as "V", obliquely in the direction shown as "O", or laterally in the direction shown as "L".

As previously discussed, the flow rate of water available for cleansing the interior of ostomy bag 50 may be advantageously adjusted so that the water emanating from nozzle 16 will strike the inside surface of ostomy bag 50 at an appropriate rate to effect optimal cleansing action. Further, large aperture 74 provides a strong downward flow of water downwards into ostomy bag 50. The pressure of the strong flow of water serves to agitate and loosen waste contained therein and to assist in evacuating the waste. It has also been determined that water having a temperature within the range of 25 to 30 degrees Celsius greatly assists in the loosening and dissolution of any solid constituents of body waste held within ostomy bag 50.

The strong stream of water flowing into ostomy bag 50 establishes water currents which force soiled water out through stoma orifice 54 of ostomy bag 50, aperture 70 of attachment appliance 39 and into the interior of housing 12, as shown. The process of simultaneously dissolving and cleansing body waste from within ostomy bag 50, especially when some form of antiseptic cleanser is provided within the water stream results in a hygienically clean ostomy bag 50.

Although the ostomy bag 50 discussed hereto has been formed with a closed bottom, it should be understood that cleaning appliance 10 may be used to clean ostomy bag 50 having various types and sizes of openings, such as a bottom opening, by suitably varying the temperature and pressure of the water flow through nozzle 16. It should also be understood that for an ostomy bag 50 having more than one opening (e.g. an opening at the bottom), it would be possible to utilize nozzle 16 having a stem which has a diameter which is substantially equal to the diameter of aperture 70 of ostomy bag 50. In such a case, soiled water would be flushed out of ostomy bag 50 through the additional openings (e.g. through a bottom or side opening).

Figure 6:
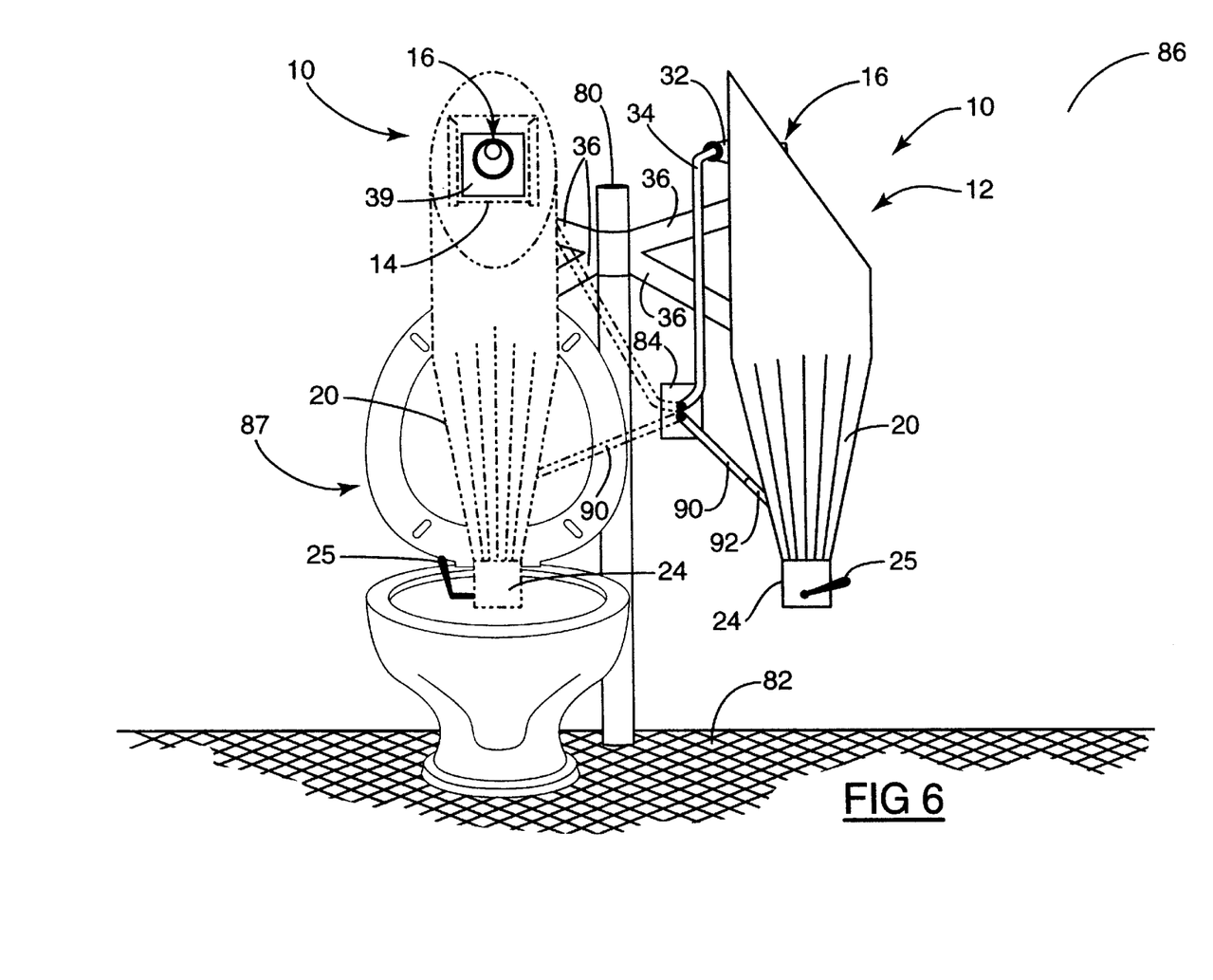
FIG. 6 is a diagrammatic view of the cleaning appliance of FIG. 1A installed within a conventional bathroom facility.

FIG. 6 shows cleaning appliance 10 in association with a typical bathroom facility. Support member 36 of cleaning appliance 10 is shown rotatably coupled to a post 80 which is installed within the flooring 82 of the bathroom. This arrangement allows the user to move cleaning appliance 10 from its storage position to its operational position (shown in dotted lines) by swinging cleaning appliance 10 around post 80.

A water mixing valve 84 can be installed within the wall 86 of the bathroom to provide a stream of water having adjustable temperature and pressure. The water flow from mixing valve 84 is directed by water tube 34 into cleaning appliance 10 as well by an additional water pipe 90 which can be used to provide water to the lower portion 20 of cleaning appliance 10 through water fixture 92. The additional stream of water provided directly to lower portion 20 assists with the flushing of soiled water from cleaning appliance 10 through outlet valve 24. In order to prepare cleaning appliance 10 for use by a particular user, a user would attach one of his or her attachment appliances 39 onto mounting plate 14 over opening 38, and insert mounting plate 14 within mounting brackets 30. The user would then attach nozzle 16 to plumbing fixture 32 through the opening 70 of attachment appliance 39.

To flush out ostomy bag 50, the user first moves cleaning appliance 10 from its storage position to its operational position such that lower portion 20 is positioned directly over a toilet 87 (shown in dotted lines) by swinging cleaning appliance 10 around post 80. The user may then remove top 28 (FIGS. 1A and 1B) from cleaning appliance 10 and open handle 25 of outlet valve 24 to allow for the eventual delivery of soiled water flow into toilet 87.

The user detaches ostomy bag 50 from his or her personal attachment appliance and inserts nozzle 16 within opening 70 of stoma mating ring 56 until it is possible to snap-fit stoma mating ring 56 onto attachment appliance 39 of mounting plate 14. Once ostomy bag 50 is secured within cleaning appliance 10, head 44 of nozzle 16 will project substantially into the ostomy bag 50. The user repositions lid 28 on housing 12 to prevent any leakage of soiled water during the cleaning process. The user then turns on mixing valve 84 and adjusts the temperature and pressure of the water depending on the type of waste to be cleansed. Plumbing fixture 32 could be a T-type fitting, so as to permit the user to inject liquid soap, detergent or deodorant into the pressurized stream water entering ostomy bag 50.

When the appropriate water flow is provided from water pipe 34 through plumbing fixture 32, the multi-directional flow of water through head 44 of nozzle 16, including the strong flow of water through large aperture 74 downwards into ostomy bag 50, will provide for improved cleaning. It has been determined that the amount of agitation and turbulence caused by the strong flow of water downwards into ostomy bag 50, along with a moderate temperature of water flow serves to break up the contents and the multi-directional flow of water causes the dissolved waste to be flushed out through stomal orifice 54 of ostomy bag 50.

Once ostomy bag 50 has been cleaned, the user turns off water mixing valve 84 and removes top 28 from housing 12 to retrieve the clean ostomy bag 50 for reuse. Finally, user closes handle 25 of outlet valve 24 and moves cleaning appliance 10 back to its storage position away from the toilet 87.

Figure 7:
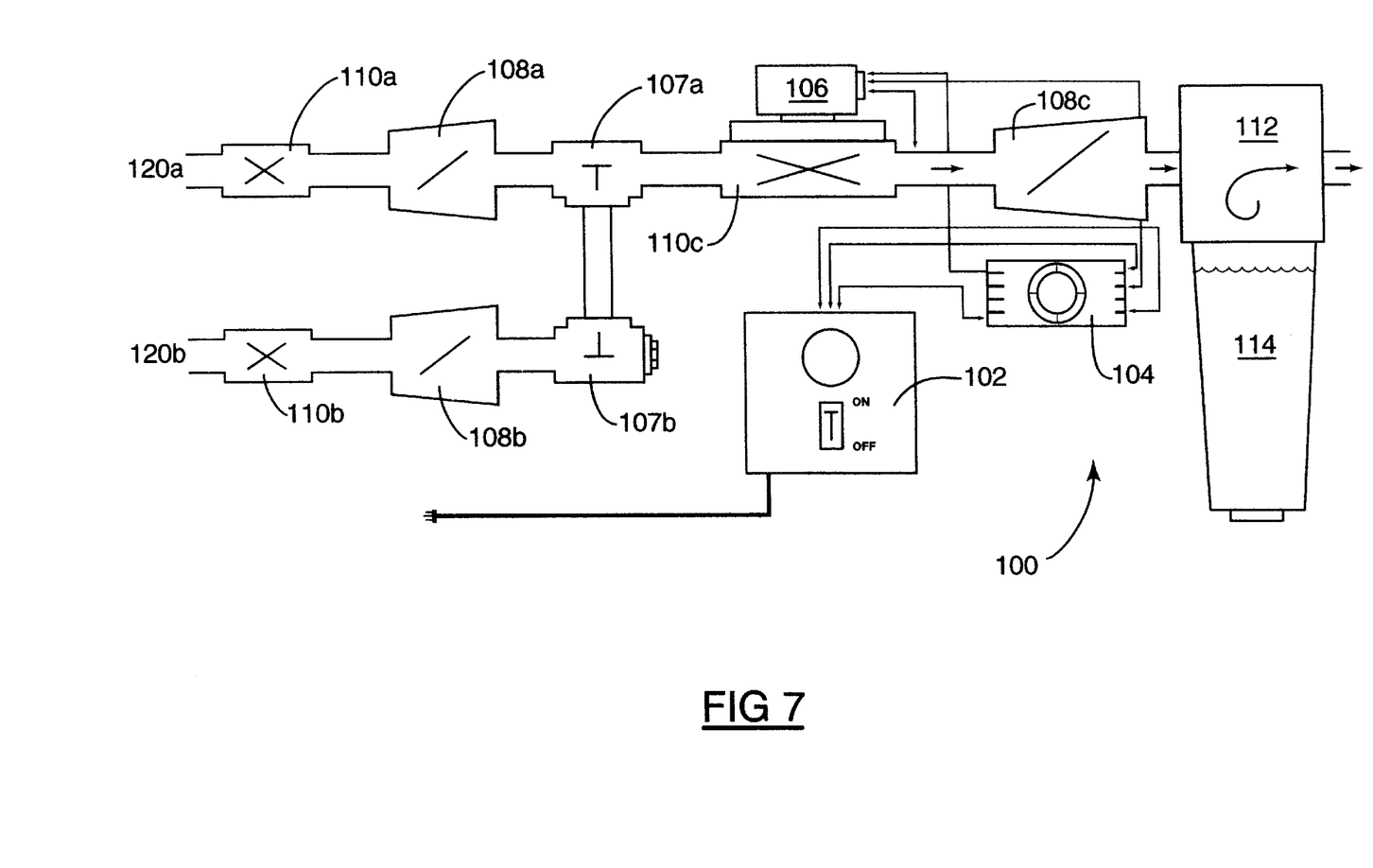
FIG. 7 is a schematic view of an automatic ostomy bag cleaning system for controlling the operation of the cleaning appliance of FIG. 1A.

FIG. 7 shows an automated controller 100 which may be used in association with cleaning appliance 10. Automated controller 100 comprises an on/off switch 102, a timer 104, solenoid switch 106, connection tees 107a, 107b, backflow preventors 108a, 108b, 108c, control valves 110a, 110b, 110c, soap injector 112 and soap container 114. It is contemplated that all the components comprising automated controller 100 be installed within a bathroom wall.

When a user wishes to begin the cleansing of an ostomy bag 50, the user simply turns on switch 102. Switch 102 then activates timer 104 which will run for a preset period of time that is suitable for the complete cleaning and disinfecting of ostomy bag 50. Specifically, timer 104 controls the amount of time that solenoid switch 106 allows control valves 110a, 110b and 110c to be open. When solenoid switch 106 is activated, an appropriate amount and proportion of hot water from inlet 120a and cold water from cold water inlet 120b is allowed through control valves .110a and 110b, backflow preventors 108a and 108b, and connection tees 107a and 107b, respectively. Backflow preventors 108a and 108b are used to prevent contamination of the soiled water from cleaning apparatus 10 into the water system.

Accordingly, the hot and cold water flows are mixed at control valve 110c, so that the resultant water flow provided to back flow preventer 108c and into cleaning appliance 10 (not shown) through soap injector 112 has an appropriate temperature and pressure. Soap injector 112 provides a predetermined amount of soap from soap container 114 into the water flow to assist with the cleansing and disinfecting of ostomy bag 50. When the cleaning cycle is over, timer 104 will trigger solenoid switch 106 to stop the flow of water through control valves 110a, 110b and 110c.

Figure 8:
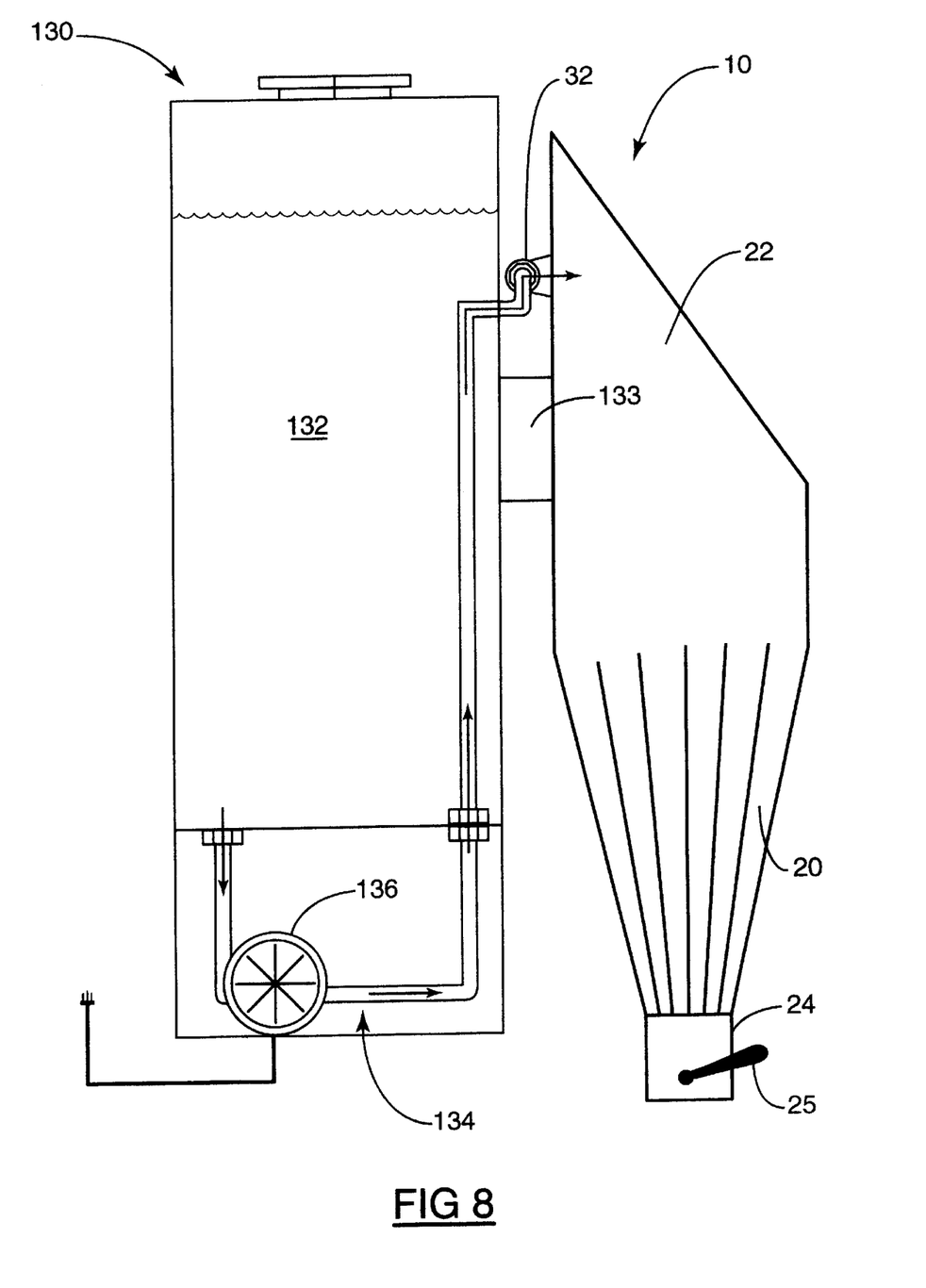
FIG. 8 is a side partial cross-sectional view of a portable ostomy bag cleaning system which incorporates the cleaning appliance of FIG. 1A.

FIG. 8 shows a portable embodiment of the invention. In the travel context, permanent connection to installed plumbing is not feasible. Accordingly, cleaning appliance 10 is connected to a portable water source 130 which comprises a reservoir 132 and a conventional water pump 134. Cleaning appliance 10 includes a bracket 133 for releasable attachment to reservoir 132 (e.g. using a conventional connector clip). Since size and weight is a factor in a portable apparatus, the components of portable water source 130 and cleaning appliance 10 are preferred to be of moulded plastic and of portable size (i.e. sized to fit within a portable carrying case).

Reservoir 132 is securely and operatively coupled to pump 134 which forces a stream of water into plumbing fixture 32 of cleaning appliance 10 and through nozzle 16 (not shown), as previously described. When using portable water source 130, it is necessary to fill reservoir 132 with water or another type of cleaning fluid before beginning the cleaning process over a toilet. Pump 134 is a conventional motorized pump and may either be electrically powered by connection to the building supply (as shown) and/or battery powered. Pump 134 includes a switch 136 which allows pump 134 to be turned on and off, once pump 134 is connected to a power source.

Portable water source 130 can be adapted to fit on top of the back of a conventional toilet facility, so that lower portion 20 of cleaning appliance 10 may be allowed to drain through outlet valve 24 over a toilet. Accordingly, reservoir 132 is held elevated above a toilet bowl (not shown) such that water flow is further motivated by gravity.

When transporting cleaning appliance 10 and portable water source 130, reservoir 132 and pump 134 are disengaged from cleaning appliance 10 and carried together in a portable carrying case. To use the portable version of cleaning appliance 10 in a conventional bathroom, the parts must be taken out of the bag, and reservoir 132 must be filled from a sink tap. Then cleaning appliance 10 is coupled to portable water source 130 and positioned over the toilet bowl, as discussed. Once pump 134 is connected to a power source, pump 134 can be activated by switch 136.

Cleaning appliance 10 allows a user to hygienically and efficiently clean an ostomy bag 50 over a conventional toilet. When cleaning appliance 10 is permanently installed within a bathroom, a user can conveniently and easily move cleaning apparatus 10 between a storage and an operational position. Since cleaning appliance 10 includes a water tight lid 28, user is protected from spillage of soiled water. For added convenience, an automatic controller can be used to control the temperature, pressure and duration of water stream within cleaning apparatus 10. Finally, cleaning apparatus 10 can also be adapted for portable use.

As will be apparent to persons skilled in the art, various modifications and adaptations of the structure described above are possible without departure from the present invention, the scope of which is defined in the appended claims.

We claim:

1. An ostomy bag cleaning appliance for cleaning an ostomy bag having a stoma mating ring, said cleaning appliance comprising:
   (a) a housing having an interior, the housing comprising an accessible upper portion having an inside surface and a lower portion configured to direct soiled water out of said housing;
   (b) a mounting plate coupled to said housing for engaging the stoma mating ring of the ostomy bag in a watertight fit, the mounting plate having an aperture in fluid communication with the interior of the housing and being spaced from the inside surface of said upper portion of said housing and having a flange extending around said aperture for enaagement with the stoma mating ring of the ostomy bag; and
   (c) a cleaning nozzle mounted within said housing and extending through said aperture of said engagement device for cleaning the ostomy bag when the stoma mating ring is engaged with said engagement device, said nozzle extending into the ostomy bag through said aperture.

2. The cleaning appliance of claim 1, wherein said aperture of said engagement device and said nozzle are shaped and sized to allow for outflow of soiled water from within the ostomy bag, through said aperture into the interior of said housing.

3. The cleaning appliance of claim 1, wherein said upper portion has an open top and a cover, said cover being shaped to cover said open top so as to form a water tight seal with said housing.

4. The cleaning appliance of claim 1, wherein said mounting plate comprises a mounting platform and an attachment appliance having an adhesive surface for affixation to the surface of said mounting platform, said attachment appliance and mounting platform when affixed together defining said aperture, said attachment appliance including the flange that extends around said aperture for engagement with the stoma mating ring of the ostomy bag.

5. The cleaning appliance of claim 4, wherein said housing includes a pair of spaced apart brackets coupled to the inside surface of said upper portion for coupling said mounting platform and said attachment appliance to said housing.

6. The cleaning appliance of claim 1, wherein said housing comprises a cylindrical upper portion and a frustoconical lower portion.

7. The cleaning appliance of claim 1, wherein said lower portion of said housing includes a valve to direct soiled water out of said housing.

8. The cleaning appliance of claim 1, wherein said nozzle has a plurality of orifices formed within.

9. The cleaning appliance of claim 8, wherein at least one of said nozzle orifices is positioned on the underside of said nozzle and is of such a relative size to the other said apertures for cleaning the ostomy bag that when said stoma mating ring of the ostomy bag is coupled to said engagement device, a substantial proportion of the water flow provided through said orifices of said nozzle is provided downwards into the ostomy bag.

10. The cleaning appliance of claim 1, comprising a support member for coupling said housing to a support pole so that said housing can be moved from an operational position over a toilet to a storage position away from the toilet.

11. The cleaning appliance of claim 1 further comprising a water source coupled to said housing to provide a flow of water to said nozzle.

12. The cleaning appliance of claim 11, further including an automatic controller, for controlling the flow of water from said water source into said housing, said controller having a timer for timing the period of operation of the water source.

13. The cleaning appliance of claim 11, wherein said water source is a bathroom water main.

14. The cleaning appliance of claim 11, wherein said water source comprises a motorized pump and a fluid reservoir.

15. An ostomy bag cleaning appliance for cleaning an ostomy bag having a stoma mating ring, said cleaning appliance comprising:

(a) a housing having an interior, the housing comprising an accessible upper portion having an inside surface and a lower portion configured to direct soiled water out of said housing;

(b) an engagement device coupled to said housing for engaging the stoma mating ring of the ostomy bag in a watertight fit, the engagement device having an aperture in fluid communication with the interior of the housing;

(c) a cleaning nozzle mounted within said housing and extending through said aperture of said engagement device for cleaning the ostomy bag when the stoma mating ring is engaged with said engagement device, said nozzle extending into the ostomy bag through said aperture;

(d) a water source coupled to said housing to provide a flow of water to said nozzle; and (e) an automatic controller for controlling the flow of water from said water source into said housing, said controller having a timer for timing the period of operation of the water source.

* * * * *